(12) United States Patent
Johnson et al.

(10) Patent No.: US 9,913,477 B2
(45) Date of Patent: Mar. 13, 2018

(54) SMALL ANIMAL REPELLENT COMPRISING AN AROMATIC SALT

(71) Applicants: Alexander O Johnson, Bartlett, TN (US); Marilyn Johnson, Collierville, TN (US)

(72) Inventors: Alexander O Johnson, Bartlett, TN (US); Marilyn Johnson, Collierville, TN (US)

( * ) Notice: Subject to any disclaimer, the term of this patent is extended or adjusted under 35 U.S.C. 154(b) by 0 days.

(21) Appl. No.: 14/941,708

(22) Filed: Nov. 16, 2015

(65) Prior Publication Data

US 2017/0273311 A1 Sep. 28, 2017

(51) Int. Cl.
| | |
|---|---|
| *A61K 9/16* | (2006.01) |
| *A01N 65/00* | (2009.01) |
| *A01N 25/12* | (2006.01) |
| *A01N 27/00* | (2006.01) |
| *A01N 59/02* | (2006.01) |

(52) U.S. Cl.
CPC ............ *A01N 65/00* (2013.01); *A01N 25/12* (2013.01); *A01N 27/00* (2013.01); *A01N 59/02* (2013.01); *A61K 9/1647* (2013.01); *A61K 9/1652* (2013.01)

(58) Field of Classification Search
CPC ............................ A61K 9/1647; A61K 9/1652
See application file for complete search history.

(56) References Cited

U.S. PATENT DOCUMENTS

| | | |
|---|---|---|
| 4,976,062 A | 12/1990 | Rutledge et al. |
| 5,104,900 A | 4/1992 | Tennyson |
| 5,705,199 A | 1/1998 | Maish |
| 6,271,533 B1 | 8/2001 | O'Brien |
| 7,011,840 B2 | 3/2006 | Wharton |
| 7,749,525 B2 * | 7/2010 | Navarro ................. A01N 31/02 106/15.05 |
| 7,749,526 B2 | 7/2010 | Goebel et al. |
| 7,846,463 B2 | 12/2010 | Johal |
| 8,962,694 B2 | 2/2015 | Dall et al. |
| 9,023,375 B2 | 5/2015 | Anderson et al. |
| 2001/0041694 A1 | 11/2001 | Clark et al. |
| 2002/0131986 A1 | 9/2002 | Clark et al. |
| 2013/0005715 A1 | 1/2013 | Kobayakawa et al. |
| 2013/0078296 A1 | 3/2013 | Grlica et al. |
| 2014/0110496 A1 | 4/2014 | Sherrill et al. |

* cited by examiner

*Primary Examiner* — Carlos A Azpuru
(74) *Attorney, Agent, or Firm* — David J. Kreher

(57) ABSTRACT

A small animal repellent wherein an aromatic compound capable of repelling small animals is infused into a salt so that the aromatic compound can be released over an extended period of time such as days or weeks.

4 Claims, 3 Drawing Sheets

SMALL ANIMAL REPELLENT COMPRISING AN AROMATIC SALT

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC

Not Applicable

DESCRIPTION

Field of the Invention

This disclosure relates to a means of repelling small animals from an area with the use of salt infused with a plurality of repelling aromatic compounds such that, the porous nature of the salt holds the plurality of repelling aromatic compound and the plurality of aromatic compounds are released over time, as the salt dissolves.

Background of the Invention

The use of aromatic compounds to repel small animals such as dogs, cats, moles, rats, mice, raccoons, reptiles, birds, and insects from an area is common in the art. If sprayed, these aromatic compounds are absorbed into the surrounding or diluted and rinsed away by rain. If the aromatic compound is spread as a powder, the spread powder is visible and makes the area appear unclean and unsightly. Thus there is a need for a long lasting small animal repellent delivery means that is not unsightly.

The present disclosure reveals a small animal repellent for repelling small animals over an extended duration by infusing a plurality of aromatic compounds into a porous medium such as salt, the saturated salt can then be spread as granules, packed in an environmental friendly pouch that can be easily spread or collected as desired, the saturated salt can be disguised within a husk to mask the presence of the small animal repellent while not interfering with the repellent's ability to repel small animals, or the environmentally friendly pouch can be disguised within a husk to mask the presence of the small animal repellent while not interfering with the repellent's ability to repel small animals. The solubility of the salt means that when the salt gets wet, the exterior coating of the salt is dissolved, which in turn releases the plurality of aromatic compounds that are infused deeper into the salt.

SUMMARY OF THE INVENTION

The present disclosure reveals a small animal repellent in the form of salt infused with a plurality of aromatic compounds. The plurality of aromatic compounds is then released over a period of days or weeks, minimizing the need for frequent reapplication. As a small animal repellent, the infused salt may be packaged in several different forms: As granules that can be spread over an area; the granules of saturated salt can be disguised within a husk to mask the presence of the small animal repellent while not interfering with the repellent's ability to repel small animals; the granules can be contained within an environmentally friendly pouch that can be spread or retrieved as desired; or the environmentally friendly pouch can be disguised within a husk to mask the presence of the small animal repellent.

DETAILED DESCRIPTION OF THE INVENTION

Figure 1:
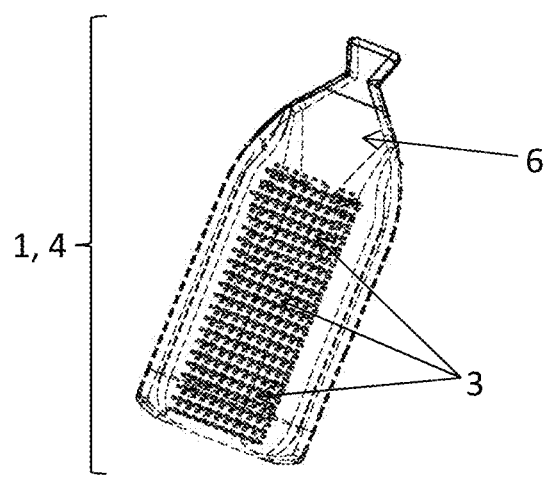
FIG. 1 is a representation of the porous nature of salt.
Figure 2:
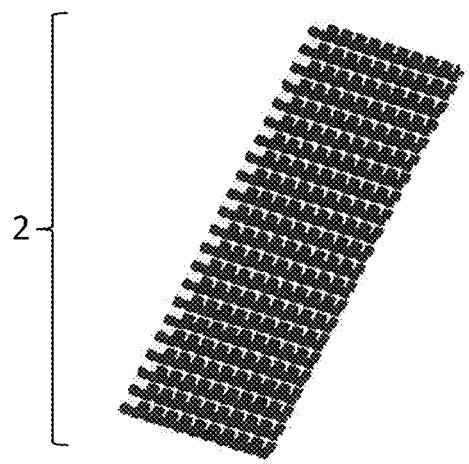
FIG. 2 is a representation of the infused salt as it would be inserted into an environmentally friendly pouch.
Figure 3:
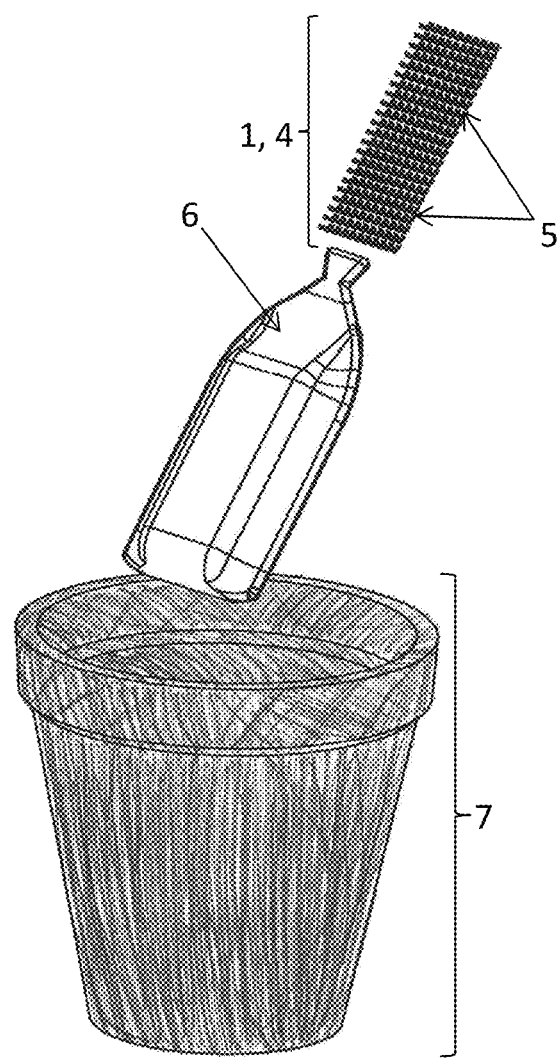
FIG. 3 is a representation of the component parts of the disclosure including the environmentally friendly pouch that would contain the infused salt, further disguised in a husk.
Figure 4:
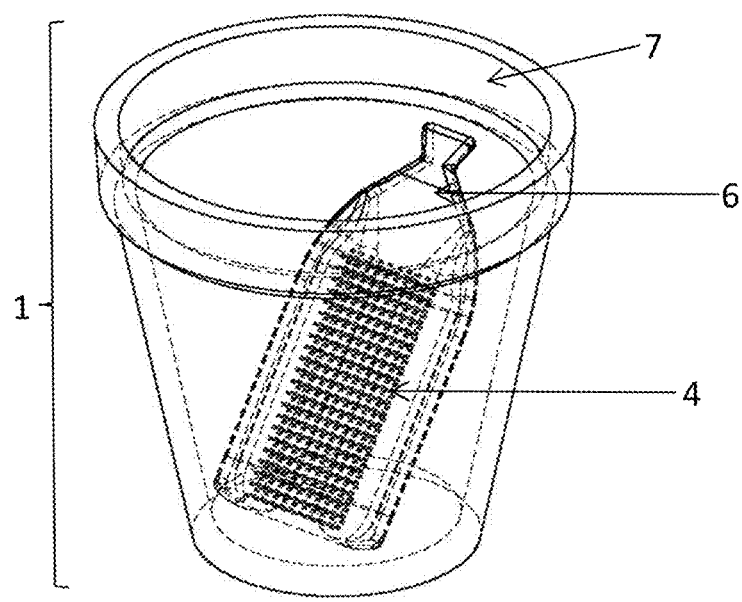
FIG. 4 is a representation of the small animal repellent including environmentally friendly pouch containing the infused salt, all within in a husk.

The present disclosure reveals a small animal repellent 1 capable of repelling small animals such as dogs, cats, rats, mice, moles, raccoons, reptiles, birds, and insects for an extended period of time comprising a salt 2 in the form of granules, a plurality of aromatic compounds 3 capable of repelling small animals, and wherein the plurality of aromatic compounds 3 is infused into the pores of the salt 2 to create an infused salt 4 such that, as the infused salt 4 dissolves, the plurality of aromatic compounds 3 are released into the air, causing small animals to be repelled from the surrounding area.

The salt 2 is a porous medium comprising such minerals as sodium chloride, sodium sulfate, magnesium chloride, magnesium sulfate, calcium chloride, calcium sulfate, potassium chloride or potassium sulfate.

The plurality of aromatic compounds 3 include but are not limited to naphthalene, sulfur, or an essential oil garlic, wheat, *capsicum*, banana, castor, agar, ajwain, *angelica* root, anise, asafoetida, balsam, basil, bergamot, bay, black pepper, buchu, birch, camphor, *cannabis* flower, caraway, cardamom, carrot seed, cedarwood, chamomile, calamus root, cinnamon, cistus species, citronella, clary sage, clove leaf, coffee, coriander, costmary, costus root, cranberry seed, cubeb, cumin, cypress, cypriol, curry leaf, davana, dill, elecampane, *eucalyptus*, fennel seed, fenugreek, fir, frankincense, galangal, *galbanum*, geranium, ginger, goldenrod, grapefruit, henna, helichrysum, hyssop, idaho tansy, jasmine, juniper berry, lavender, *laurus nobilis*, ledum, lemon, lemongrass, *litsea cubeba*, majoram, *melaleuca*, melissa (lemon balm), *mentha arvensis*, mountain savory, mugwort, mustard, myrrh, myrtle, neem tree, neroli, nutmeg, orange, oregano, orris, palo santo, parsley, patchouli, *perilla*, pennroyal, peppermint, petitgain, pine, ravensara, red cedar, roman chamomile, rose, rosehip, rosemary, rosewood, sage, star anise, sandalwood, *sassafras*, savory, schisandra, spearmint, spikenard, spruce, tangerine, tarragon, tea tree, thyme, *tsuga*, turmeric, valerian, vetiver, western red cedar, wintergreen, yarrow, ylang-ylang, zeodary and parts thereof.

The infused salt 4 can be packaged to be distributed as granules 5, in an environmentally friendly pouch 6 that lets moisture in and allows the plurality aromatic compounds 3 infused into the infused salt 4 to be released into the air, or the environmentally friendly pouch 6 can be further disguised in a husk 7 to make the small animal repellent 1 less noticeable. The environmentally friendly pouch 6 is made from a fabric capable of breaking down over time by exposure to natural weather conditions. The husk 7 is made of a material capable of disguising the contained environmentally friendly pouch 6 in the outdoors, such as coconut husk, fibrous wood material, or a porous plastic.

What is claimed:

1. A small animal repellent capable of repelling small animals for an extended period of time comprising:
   a salt in the form of granules;
   a plurality of aromatic compounds capable of repelling small animals; and
   wherein the plurality of aromatic compounds is infused into the pores of the salt to create an infused salt such that, as the salt dissolves, the plurality of aromatic compounds is released into the air.

2. The small animal repellent of claim 1 wherein the infused salt is disguised a husk to make the small animal repellent less noticeable.

3. The small animal repellent of claim 1 wherein the infused salt is packaged in an environmentally friendly pouch that lets moisture in and allows the plurality aromatic compounds infused into the salt to be released into the air.

4. The small animal repellent of claim 3 wherein the environmentally friendly pouch is further disguised in a husk to make the small animal repellent less noticeable.

* * * * *